(12) United States Patent
Sobe

(10) Patent No.: US 10,390,889 B2
(45) Date of Patent: Aug. 27, 2019

(54) REMOVABLE NAVIGATION SYSTEM AND METHOD FOR A MEDICAL DEVICE

(75) Inventor: Lior Sobe, Kadima (IL)

(73) Assignee: ST JUDE MEDICAL INTERNATIONAL HOLDING S.Á R.L., Luxembourg (LU)

(*) Notice: Subject to any disclaimer, the term of this patent is extended or adjusted under 35 U.S.C. 154(b) by 0 days.

(21) Appl. No.: 12/843,095

(22) Filed: Jul. 26, 2010

(65) Prior Publication Data

US 2012/0017923 A1 Jan. 26, 2012

(51) Int. Cl.
*A61B 17/00* (2006.01)
*A61B 34/20* (2016.01)

(52) U.S. Cl.
CPC .... *A61B 34/20* (2016.02); *A61B 2017/00053* (2013.01); *A61B 2017/00477* (2013.01); *A61B 2034/2051* (2016.02)

(58) Field of Classification Search
CPC ........ A61B 17/12022; A61B 17/12136; A61B 5/0031; A61B 5/6862; A61B 2560/0219; A61B 5/0002; A61B 5/076; A61B 19/5244; A61B 2019/5251; A61N 1/057; A61N 1/0573; A61M 25/0169; A61M 25/0172
USPC .... 623/1.11; 604/270, 523, 529, 500, 96.01, 604/164.03; 600/112, 9–13, 422–424; 128/899; 606/129; 607/115, 116, 607/126–128
See application file for complete search history.

(56) References Cited

U.S. PATENT DOCUMENTS

| | | | |
|---|---|---|---|
| 4,913,164 A * | 4/1990 | Greene et al. | 607/126 |
| 5,040,548 A | 8/1991 | Yock | |
| 5,163,911 A | 11/1992 | Sirimanne et al. | |
| 5,318,532 A * | 6/1994 | Frassica | A61M 25/1002 604/913 |
| 5,329,935 A | 7/1994 | Takahashi | |
| 5,353,795 A | 10/1994 | Souza et al. | |
| 5,598,844 A | 2/1997 | Diaz et al. | |
| 5,603,694 A * | 2/1997 | Brown et al. | 604/500 |
| 5,645,533 A | 7/1997 | Blaeser et al. | |
| 5,833,608 A | 11/1998 | Acker | |
| 5,868,741 A * | 2/1999 | Chia et al. | 606/41 |
| 5,935,098 A | 10/1999 | Blaisdell et al. | |
| 6,126,647 A * | 10/2000 | Posey et al. | 604/270 |

(Continued)

FOREIGN PATENT DOCUMENTS

EP 0371486 A1 6/1990
JP 2001-275942 A 10/2001

(Continued)

OTHER PUBLICATIONS

"International Search Report and Written Opinion", PCT/US2011/040034 dated Oct. 18, 2011.

*Primary Examiner* — Martin T Ton
(74) *Attorney, Agent, or Firm* — Dykema Gossett PLLC

(57) ABSTRACT

A removable navigation system for a medical device configured for insertion within a lumen in a body is provided. The removable navigation system includes a sheath operatively configured to cover at least a portion of the medical device, a positioning sensor affixed to the sheath and a deformable fixation element disposed between the sheath and the medical device. The deformable fixation element is operatively deformed to temporarily fix a position of the medical device relative to the sheath and positioning sensor.

27 Claims, 6 Drawing Sheets

(56) References Cited

U.S. PATENT DOCUMENTS

| | | | |
|---|---|---|---|
| 6,179,811 B1* | 1/2001 | Fugoso et al. | 604/96.01 |
| 6,216,026 B1 | 4/2001 | Kuhn et al. | |
| 6,233,476 B1 | 5/2001 | Strommer et al. | |
| 6,442,413 B1* | 8/2002 | Silver | 600/345 |
| 6,533,772 B1 | 3/2003 | Sherts et al. | |
| 6,628,980 B2* | 9/2003 | Atalar | A61B 1/00154 |
| | | | 324/318 |
| 7,097,643 B2* | 8/2006 | Cornelius et al. | 606/32 |
| 7,197,354 B2 | 3/2007 | Sobe | |
| 7,684,873 B2* | 3/2010 | Gerber | 607/116 |
| 8,504,139 B2 | 8/2013 | Jacobsen et al. | |
| 2002/0143317 A1 | 10/2002 | Glossop | |
| 2004/0097804 A1 | 5/2004 | Sobe | |
| 2004/0220471 A1* | 11/2004 | Schwartz | 600/424 |
| 2004/0230282 A1* | 11/2004 | Cates et al. | 607/126 |
| 2006/0206170 A1* | 9/2006 | Denker et al. | 607/60 |
| 2007/0093710 A1* | 4/2007 | Maschke | 600/407 |
| 2007/0118079 A1 | 5/2007 | Moberg et al. | |
| 2007/0208252 A1* | 9/2007 | Makower | 600/424 |
| 2008/0091193 A1* | 4/2008 | Kauphusman et al. | 606/41 |
| 2008/0171989 A1* | 7/2008 | Bell | A61M 25/0662 |
| | | | 604/170.02 |
| 2008/0287907 A1* | 11/2008 | Gregory et al. | 604/500 |
| 2009/0062772 A1 | 3/2009 | Wakeford et al. | |
| 2009/0082609 A1 | 3/2009 | Condado | |
| 2009/0112221 A1* | 4/2009 | Burke et al. | 606/102 |
| 2009/0182278 A1 | 7/2009 | Eversull et al. | |
| 2010/0106011 A1* | 4/2010 | Byrd et al. | 600/424 |
| 2011/0282144 A1* | 11/2011 | Gettman | A61B 1/041 |
| | | | 600/109 |
| 2013/0317355 A1 | 11/2013 | Jacobsen et al. | |

FOREIGN PATENT DOCUMENTS

| | | |
|---|---|---|
| WO | WO 97/29679 A2 | 8/1997 |
| WO | 2007005976 A1 | 1/2007 |

* cited by examiner

REMOVABLE NAVIGATION SYSTEM AND METHOD FOR A MEDICAL DEVICE

BACKGROUND OF THE INVENTION a. Field of the Invention

The present disclosure generally relates to a removable navigation system for a medical device and a navigation method for a medical device within a body. In particular, the present disclosure relates to a system in which a medical device is at least partially covered by a sheath having a positioning sensor affixed thereto and in which a deformable fixation element is used to temporarily fix a position of the sheath and positioning sensor relative to the medical device.

b. Background Art

It is well known that various diagnostic and treatment procedures are performed by inserting a medical device, such as but not limited to, a catheter, guide wire or lead, through a lumen of a body of a patient, such as a blood vessel in the circulation system, the gastrointestinal tract, the brain vessels, the bronchial tree, and the like. When a surgeon is performing an operation on an artery or a vein, such as, but not limited to, angioplasty or implanting a stent within an artery, it is often necessary for the surgeon to know the position and the orientation of the tip of the inserted medical device during the operation. The position and orientation of the medical device can be determined using a variety of components affixed the medical device such as but not limited to, an electromagnetic sensor, ultrasonic sensor, or a marker attached to the medical device (e.g., a radiopaque marker).

One example of a system for determining the position and orientation of a medical device as it advances to the target location is system sold under the registered trademark "ENSITE NAVX" by St. Jude Medical, Inc. EnSite is capable of displaying 3D positions of multiple catheters. This is achieved by applying a low-level 5.6 kHz current through orthogonally-located skin patches. The recorded voltage and impedance at each catheter's electrodes generated from the low level 5.6 kHz current allows the catheter's distance from each skin patch, and ultimately, their location in space, to be triangulated with the help of a reference electrode. Three-dimensional images of each catheter can then be displayed. Respiratory motion artifact can also be eliminated to prevent confounding of actual catheter position. With respect to cardiac related procedures, heart chamber geometry can be determined thereafter by moving a mapping catheter along the endocardial surface.

The inventors herein have recognized a need for a removable navigation system for a medical device and a navigation method for a medical device within a body that will improve upon known systems and methods for tracking internal medical devices.

BRIEF SUMMARY OF THE INVENTION

It is desirable to be able to provide a removable navigation system for a medical device and an improved navigation method for a medical device.

A removable navigation system for a medical device configured for insertion within a lumen in a body includes a sheath operatively configured to cover at least a portion of the medical device and a positioning sensor affixed to the sheath. The system further includes a deformable fixation element disposed between the sheath and the medical device, the deformable fixation element operatively deformed to temporarily fix a position of the medical device relative to the sheath and positioning sensor.

A navigation method for a medical device within a body includes the steps of inserting the medical device into a sheath. A positioning sensor is affixed to the sheath. The method further includes the step of deforming a deformable fixation element disposed between the sheath and the medical device to temporarily fix a position of the medical device relative to the sheath and positioning sensor. The method further includes the steps of guiding the medical device and sheath to a location within a lumen of a body and monitoring a position of the positioning sensor within the body.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
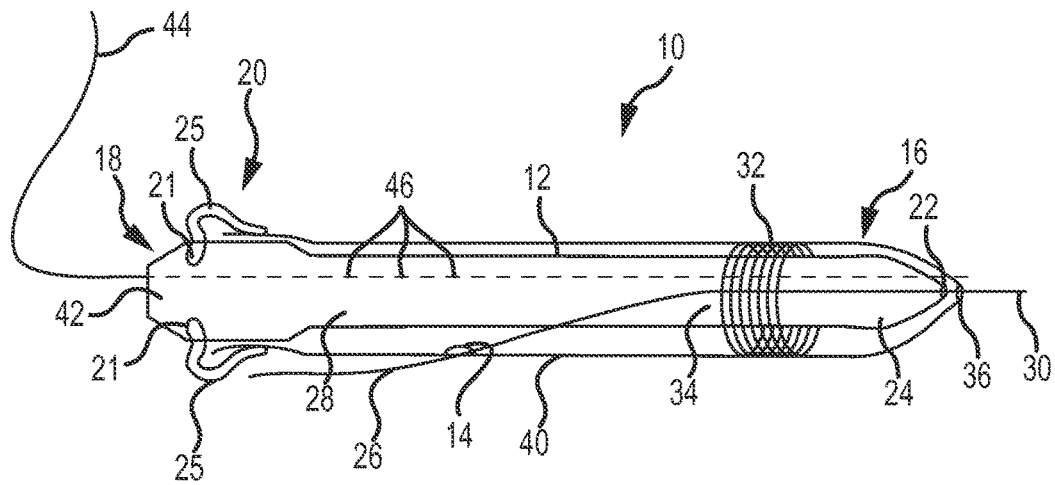
FIG. 1 is a first embodiment of the removable navigation system of the present disclosure where the fixation element may be a shape memory alloy.

Integrating position sensing hardware with conventional medical devices such as catheters, guide wires and leads used in lumens of bodies is difficult for a number of reasons. First, embedding a coil, cable, transmitter and the like can be quite costly due to the complex structure of a medical device having such embedded components. The design, manufacture and production of such an embedded medical device requires significant development time and effort. In contrast, regulatory limitations may require a quick and low cost solution in a short time frame.

Second, the dimensions and mechanical properties of the medical device may also change and be compromised once a sensor is added into the medical device. In one example, a catheter may become less flexible as a result of adding a sensor thereby making it difficult for a user to perform a particular procedure once the catheter reaches the target site.

In particular, some navigation systems which implement magnets may typically improve a catheter's trackability. However, those same materials used for navigation may not be beneficial upon treatment, in that the navigation materials may make a catheter less flexible for diagnoses and/or treatment. In another example, the permanent embedding of a sensor in a medical device may result in an increased diameter for the medical device due to the embedment of a hollow coil over a catheter's outer tube or may be undesirable for clinical reasons.

Third, existing navigation systems often require non-biocompatible materials. The coils, cables, and termination that are used for catheter navigation systems all generally contain non-biocompatible materials such as copper, silver, nickel alloy, etc. Accordingly, in the case of an implantable device, it is a major advantage to have those components on or within a removable sheath.

Fourth, existing navigation systems frequently are incompatible with the function and operation of the medical device with which they will be used. For example, an ablation catheter may be constructed of various components that are not suitable for integration with a navigation system. The catheter may require the ability to transmit high energy levels and therefore, may be incompatible with the components of a navigation system such as an electromagnetic coil. For example, in a cardiac ablation procedure, the electrodes at the tip of the catheter or medical device gathers data and a variety of electrical measurements are made. The data pinpoints the location of the faulty electrical site to confirm that the site is damaged. Accordingly, the medical device transfers high levels of energy to destroy a small amount of tissue thereby ending the disturbance of electrical flow through the heart and restoring a healthy heart rhythm. The energy may take the form of radiofrequency energy, which cauterizes the tissue, or intense cold, which freezes, or cryoablates the tissue or other conventional ablation energies. However, given the very high and/or very low operating temperatures for an ablation catheter, it may be difficult or costly to implement an embedded navigation sensor in the medical device.

In light of the cost and complexity issues associated with implementing a permanent navigation system in a medical device, there is a need to temporarily enable existing medical devices and implants with navigation capabilities, while minimizing the effect of the navigation system on the intended performance of the medical device. Therefore, in order to reconcile the material and physical incompatibles as well as the costly nature of having a navigation system integrated into the medical device, the present disclosure implements a low cost, removable navigation system on a medical device. The disclosed technique overcomes the disadvantages of the prior art by providing a method for temporarily turning a medical device, which is not navigationally enabled, into a navigationally enabled device, while minimizing alterations to the medical device itself.

Referring to FIG. 1, a removable navigation system 10 for a medical device 12 is provided. The medical device 12 is configured for insertion within a lumen in a body such as a blood vessel. The system includes a sheath 40, a positioning sensor 32 and a deformable fixation element 20.

In the illustrated embodiment, the medical device 12 comprises a catheter. A catheter is a tube that is inserted into a body cavity (not shown), duct (not shown) or vessel (not shown). Catheters thereby allow drainage, injection of fluids or access by surgical instruments as indicated above. It should be understood, however, that system 10 may find use with other medical devices including guide wires, electrical leads, a stent, a stylet, or a needle. The medical device 12 may typically have an elongate shape and include a distal end 16 and a proximal end 18. Device 12 may be tubular and define a lumen 22 open at one end. The open lumen 22 allows for the delivery of food, access by surgical instruments, or the drainage of fluid from the opening at the distal end 16 of device 12. In the illustrated catheter embodiment, the medical device 12 also includes a hub 42 which may be located at proximal end 18.

The catheter may be formed of any suitable tubing. Portions of the catheter, such as a portion 24 proximate the distal end 16, may be made from a relatively soft material having a flexural modulus. The soft material at the distal end 16 and at the region proximal to the distal end 16 allows the catheter 12 to be atraumatic. Stiffer material in the region 28 between the proximal end 18 and the region proximal to the distal end 16 allows the catheter to have greater pushability and maneuverability during insertion than if a softer material was included in this region of the catheter. The stiffer region 28 of the catheter may have a flexural modulus which is generally greater than the area having relatively soft material.

The walls of the catheter may contain a reinforcing material. The walls of a catheter may contain an MRI compatible reinforcing material such as a fiber, monofilament, or non-ferrous metal. This allows the catheter to have a thin wall, while maintaining the desired inner diameter. A reinforcing material in the catheter may also provide kinking-resistance or crush-resistance to the catheter as the catheter is traveling through or within a patient's body. A reinforcing material within the catheter also allows the catheter to be especially resistant to tearing, thereby facilitating the use of a plunger to purge a clogged catheter without risk of damaging the catheter, even when the catheter is conforming to a tortuous path within a patient's body. Suitable reinforcing materials are stiff, MRI-compatible, i.e. non-ferrous materials such as, polyester, copper, aluminum, non-magnetic steel, or other non-ferrous material is polyester monofilament. However, the reinforcing material can by any stiff non-ferromagnetic material such as copper or other monofilament materials. It is also to be understood that a combination of nonstiff material may also lead to a stiff section by constructing or concentrating the nonstiff material in a manner wherein the nonstiff material is operatively configured to be shaped or interact in a manner that stiffens the section.

Because the catheter or another medical device may be bulky, it may be difficult to guide the catheter to the target operational site on its own. For this purpose, a guide wire 26 whose diameter is substantially smaller than that of the catheter, is guided through the body lumen to the operational site before inserting the catheter, and then the catheter is passed over the guide wire 26 and guided to the target operational site.

Methods and systems for maneuvering the guide wire 26 through a lumen of a patient to the operational sites, are known in the art. Generally, an operator manipulates the movements of the guide wire 26 by manually pushing or pulling the guide wire 26 or twisting the guide wire 26, while he watches an image of the tip of the guide wire 26 against a real time two-dimensional image of the lumen (e.g. by employing fluoroscopy angiogram). In this manner, the tip of the guide wire 26 may be maneuvered at various bifurcations of the lumens, in order to reach the target operational site. The same method is employed for manipulating a catheter, only that a marker (e.g. an X-ray opaque material) may be located within a distal end of the catheter.

The guide wire 26 may be inserted through a site such as, but not limited to the groin or neck of a patient. The guide wire 26 may be routed to a target site within the patient's body. The guide wire 26 may be formed from stainless steel, nitinol, polymers, braided polymers or the like.

A medical device 12 in accordance with the present invention may be located using guide wire 26 in one of two ways: (1) the "over-the-wire" guide wire method; and (2) the rapid-exchange method. In the "over the wire" method, device 12 is mounted over the guide wire 26, the guide wire 26 extending inside device 12 throughout its length. As the distal end 16 of device 12 and the distal end of the guide wire 26 are located inside the body, the operator advances device 12 over the guide wire 26 by pushing device 12 from its proximal end 18, which is outside the patient's body.

In the "rapid-exchange" (sometimes also called "monorail" or Single Operator Exchange—SOE) catheterization method, device 12 is engaged to the guide wire 26 through the open end of lumen 22 at distal end 16, whereas most of the body of device 12 lies adjacent the guide wire 26 (but not over it), so that the device 12 can be quickly replaced with another (hence the name "rapid-exchange"). The guide wire exit port on the catheter should be aligned with a guide wire exit port 14 located on the sheath (i.e. the sheath has to have a designated area with a hole (cut-out shown as guide wire exit port 14) specially designed to allow the guide wire to pass through.

Although a guide wire clip (not shown) may be implemented, a torque device may be used to stir and rotate the guide wire. The guide wire is followed by a catheter (the small diameter, thin wall flexible tube) which is then inserted through a small hole made in an area such as the femoral artery in the groin area. The guide wire is then slowly fed through the femoral artery hole and then is slowly maneuvered though the vascular system to an operating site. In moving toward the site, the guide wire is often steered around sharp corners and through small openings. The steering may be done by using a guide wire with a bend at the tip and by rotating the wire or "torqueing" the wire and feeding the wire forward as it is carefully maneuvered into position.

In sum, guide wire 26 may be used to direct device 12 to the target site within a patient's body. The guide wire 26 is initially inserted into the body lumen and a user is required to navigate the distal end 30 of the guide wire 26 to the target location (and even some distance further beyond). Once the guide wire 26 reaches the target location, the catheter or other medical device 12 is engaged to the guide wire 26 and advanced to the target location.

According to the present disclosure, a removable sheath 40 is externally installed over the medical device 12 (e.g., a catheter). The removable sheath 40 may be made out of polymers, a polymer and braid combination, a stainless steel hypotube, nitinol hypotube, or a combination of the foregoing or like material or combinations of like material. Such materials may be designed with varying degrees of trackability and torque. Moreover, these materials can be made to resist kinking in the most intricate, demanding medical procedure.

The removable sheath 40 may be tubular and may conform with the inner or outer contour of the medical device 12 to facilitate the ease of guiding the medical device 12 through the patient's body to the target site. Also, as shown in FIG. 1, the sheath 40 may have an open lumen 36 extending between first and second openings located at the proximal and distal ends of the sheath 40 which allows the distal end 30 of the guide wire 26 to pass through the sheath 40

Figure 5:
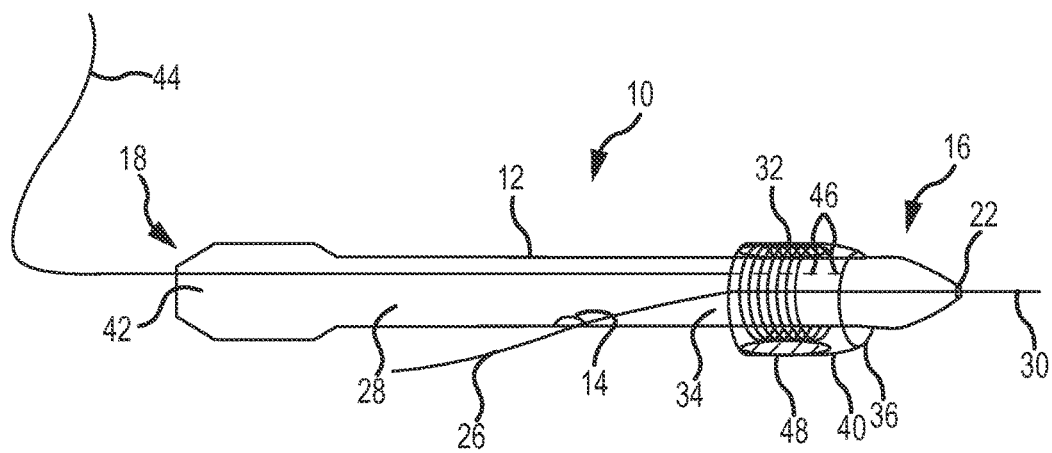
FIG. 5 is a fifth embodiment of the removable navigation system of the present invention where the sheath only covers a portion of the medical device.

The sheath 40 of the present disclosure is operatively configured to cover at least a portion of a medical device 12. Referring to FIG. 1, in a non-limiting example, the sheath 40 may cover or enclose the medical device 12. Alternatively, as shown in FIG. 5, the sheath 40 may cover only a portion of the medical device 12. The covered portion of the medical device 12 may be the distal end 16, a portion 34 of the medical device 12 intermediate the distal end 16 and proximal end 18 (as shown in FIG. 5), the proximal end 18, or a combination of areas of the medical device 12.

The sheath 40 is operatively configured to be removed from the medical device 12 while the sheath 40 and medical device 12 are disposed within the lumen of the body in the case, for example, where the medical device is to be implanted within the body. Referring to FIG. 1, in one non-limiting example, the sheath 40 may have perforations 46 which allow the sheath 40 to be easily removed from the medical device 12 once the medical device 12 reaches the target area. The perforations 46 allow the sheath 40 to easily break apart at the perforations 46 when a user pulls the sheath 40 away from the medical device 12. As shown in the illustrated embodiment, perforations 46 are disposed longitudinally along sheath 40. It should be understood, however, that perforations 46 could be arranged in different patterns. The perforation is used to cut the sheath in half in cases such as lead placement for a pacemaker or CRT.

Figure 2A:
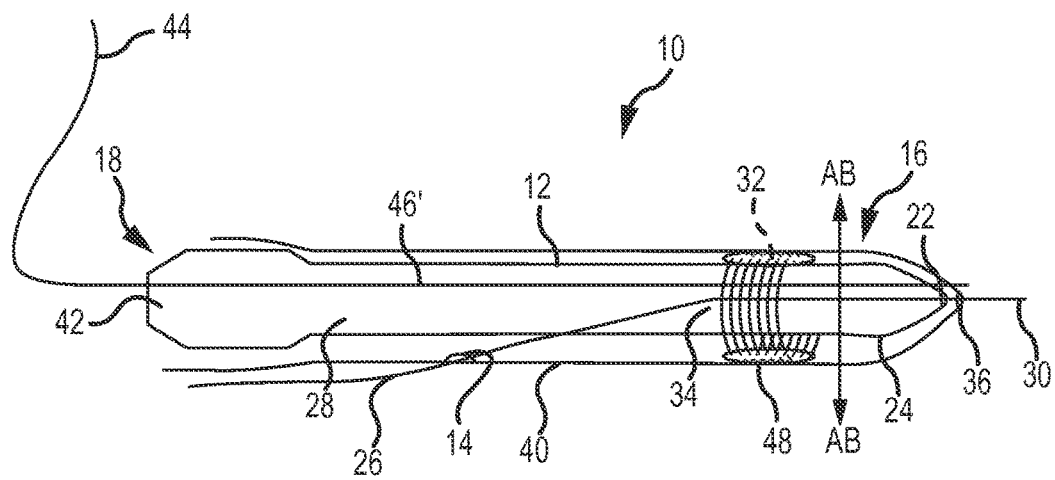
FIG. 2A is a second embodiment of the removable navigation system of the present invention where the fixation element is a pressurized ferrule.

Different arrangements of perforation can be applied as long as we achieve the desired outcome. Such non-limiting examples of perforations include: (1) a spiral perforation that travels along the longitudinal direction of the sheath; (2) circumferential perforations; (3) a longitudinal perforation and a combination of longitudinal, circumferential and/or spiral perforations. Referring now to FIG. 2A, in another non-limiting example, the sheath 40 may have a weakened area 46' where the sheath 40 thickness is smaller than the overall sheath thickness along the longitudinal direction of the sheath. Upon reaching the target site in the patient's body, the sheath 40 may be easily removed from the medical device 12 by pulling the sheath 40 away from the medical device 12. The weakened area 46' of the sheath 40 allows the sheath 40 to break apart so that the sheath 40 may be removed. The sheath 40 may include an extended section 44 or portion that remains outside of the patient's body thereby allowing a user to pull on the sheath 40 so that the sheath 40 breaks away from the medical device 12.

In an alternative embodiment, a blade (not shown) may be coupled with the medical device 12 to pierce the sheath 40 to allow for extraction of the sheath 40 from the patient's body. The blade may comprise a commercially available slitter such as the St. Jude Medical CPS™ Slitter. Cutting starts at the proximal end of the device, or in this non-limiting example, the catheter hub. The blade is kept stationary with one hand and the sheath to be cut is pulled out of the body with other hand towards the physician torso. The slitting cuts the sheath in half releasing it from the body leaving the medical device or catheter in the body.

The removable navigation system 10 may also include a positioning sensor 32. The positioning sensor 32 may be disposed or embedded within the sheath 40 material (as shown in FIG. 1). Alternatively, the positioning sensor 32 may be affixed to the interior or the exterior of the sheath 40. A non-limiting example of a positioning sensor 32 of the present disclosure may be a hollow electromagnetic coil as shown in FIG. 1. The positioning sensor 32 may surround the medical device 12 and communicate with the navigation system 10 to notify the user of the location of the medical device 12. Conductors would extend along or in the sheath back to an external signal processing unit. The coil can be passive and measure induced voltage generated by the magnetic field. It requires transferring the signal either by a form of conductor or wirelessly.

The removable navigation system 10 of the present disclosure further includes a deformable fixation element 20. Upon deformation, the fixation element 20 temporarily affixes the sheath 40 to the medical device 12, to eliminate relative motion there between, during the navigation process of the medical device 12 to the target site. The fixation element 20 may be disposed on the sheath 40 or may be disposed on the medical device 12. It is to be understood that the fixation element 20 may be positioned proximally or distally to the sensor 32. The fixation element 20 may also be positioned at the sensor 32 as shown in FIG. 2A. Upon actuation or engagement, the fixation element 20 is operatively configured to engage the sheath 40 to the medical device 12 in order to maintain the sheath 40 into its position on the medical device 12. The fixation element 20 may surround the entire circumference of medical device 12 or only a portion thereof.

The fixation element 20 may assume a variety of forms. Referring to FIG. 1, the fixation element may comprise a shape memory alloy 25 such as Nitinol. The shape memory alloy 25 may be configured in the manufacturing process so that it locks the sheath 40 to the medical device 12 when the shape memory alloy is actuated. The sheath 40 may be pulled back in a way that will expose the shape memory alloy 25 in a manner that causes the shape memory alloy to lock the sheath 40 on the device 12. In order to release the connection between the removable sheath 40 and medical device, the sheath 40 may be pushed back into place. Alternatively, the contained shape memory alloy may be pushed out from a lumen 21 in the medical device 12 to fixate the sheath 40 and then pulled back from the lumen 32 to release the lock on the sheath 40.

Figure 2B:
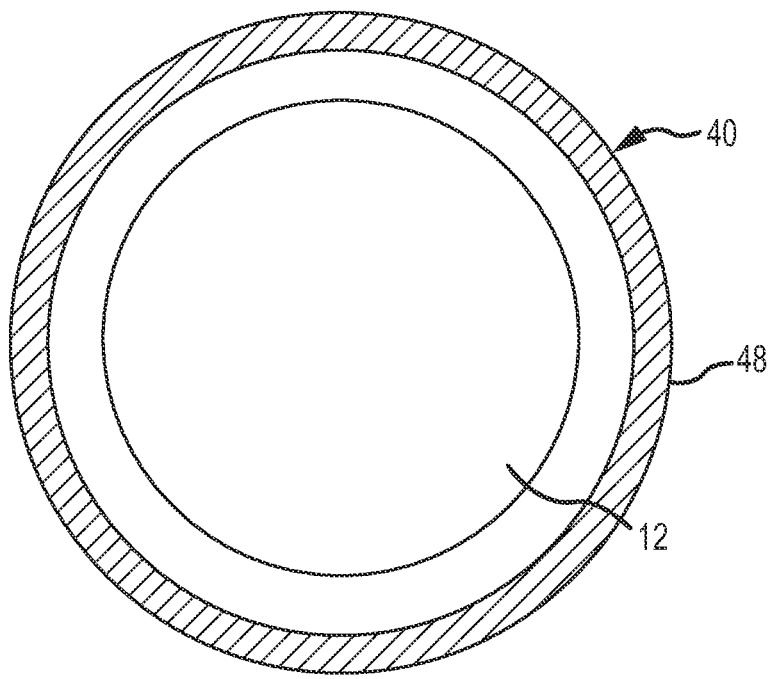
FIG. 2B is a cross section of the second embodiment along lines AB in FIG. 2A where the ferrule is not pressurized.
Figure 2C:
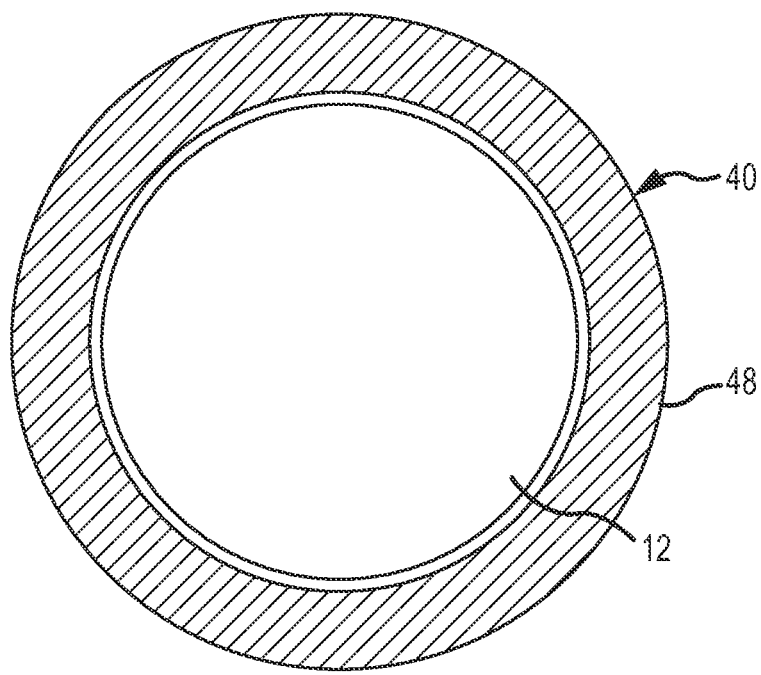
FIG. 2C is a cross section of the second embodiment along lines AB in FIG. 2A where the ferrule is pressurized.

Referring to FIGS. 2A, 2B and 2C, the fixation element 40 may alternatively comprise pressurized ferrule 48. A ferrule 48 may be implemented by applying pressure on a side of a polymeric washer such that it will expand on its outer diameter and shrink about its inner diameter. FIG. 2B illustrates a cross-sectional view of the medical device 12, the sheath 40 and the ferrule 48 along lines AB in FIG. 2A before the ferrule 48 expands. The sheath 40 may be integral with or affixed to the outer side of the ferrule. FIG. 2C illustrates the same cross section along lines AB of FIG. 2A when the ferrule is pressurized and expands such that the sheath 40 will not move relative to the medical device 12 due to the expanded ferrule 48 holding the sheath 40 in place.

Figure 3:
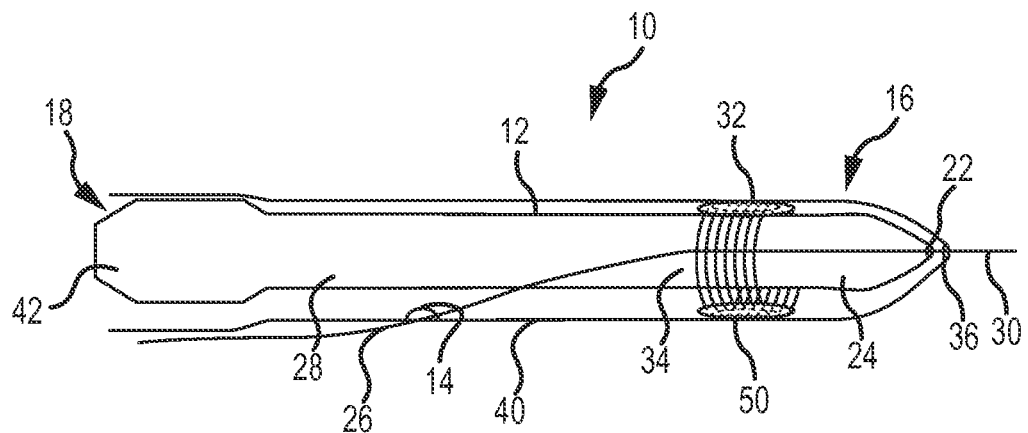
FIG. 3 is a third embodiment of the removable navigation system of the present invention where the fixation element is circumferential and inflatable.
Figure 4:
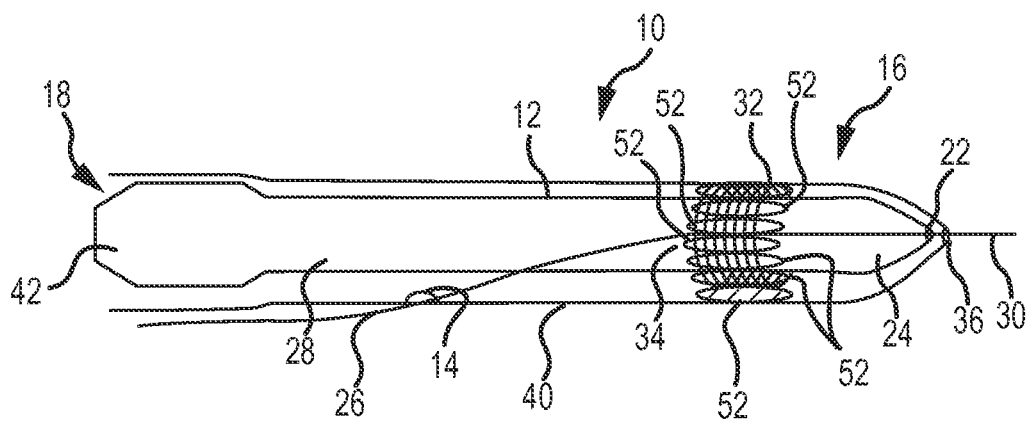
FIG. 4 is a fourth embodiment of the removable navigation system of the present invention where the fixation element is an array of balloons.

Referring to FIG. 3, the fixation element 20 may be an inflatable balloon 50 or other expandable/collapsible element that may expand to secure the sheath 40 in position and contract to release the sheath 40 from position. The inflatable balloon 50 may be positioned on the internal wall of the sheath 40 at the sensor 32 area (proximally, distally, or at). The inflatable balloon 50 (shown in FIG. 3) may surround the medical device 12. It is also to be understood that an array of small balloons 52 (shown in FIG. 4) may be located circumferentially such that once expanded, the array of balloons lock the sheath 40 into place.

Figure 6:
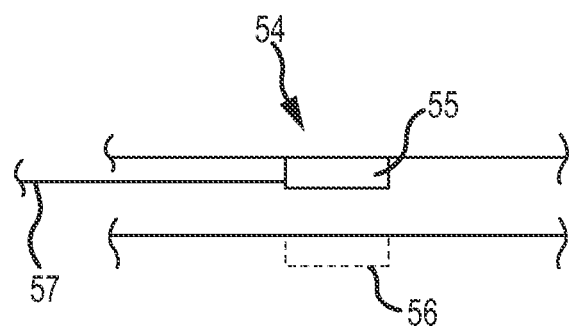
FIG. 6 is a sixth embodiment of the removable navigation system of the present invention where the fixation element is a mechanical locking device.

Referring to FIG. 6, the fixation element 20 may alternatively comprise a mechanical locking device 54. Device 54 is configured to cooperate with a corresponding structure mounted on, projecting from, or formed in the body of device 12. For example, device 54 may comprise a one or more tabs 55 configured to engage corresponding detents 56 in device 12. Device 54 may alternatively comprise pincers configured to engage corresponding apertures in the body of device 12. Device 54 may be deformed or actuated by movement of a pull wire 57 extending from device 54 through sheath 40 to the proximal end of sheath 40. It should be understood that the particular mechanical structures described above are exemplary only and a variety of deformable mechanical structures could be used to lock sheath 40 and device 12 into position relative to one another. Further, it should be understood that the relative positions of various mechanical locking components could be reversed as to the sheath 40 and device 12 (e.g., with tabs 55 on device 12 engaging detents 56 formed in sheath 40).

Figure 7:
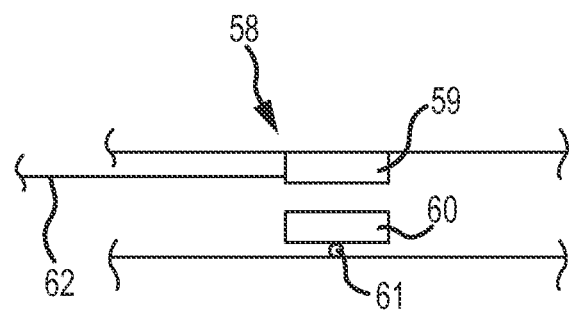
FIG. 7 is seventh embodiment of the removable navigation system of the present invention where the fixation element is an electromechanical locking device.

Referring to FIG. 7, the fixation element 20 may alternatively comprise an electromechanical locking device 58. Device 58 is again configured to cooperate with a corresponding structure mounted on, projecting from, or formed in the body of device 12. For example, device 58 may comprise a one or more electromagnets 59 configured to draw a ferromagnetic structure 60 into engagement with the electromagnets 59 upon energization of the electromagnets 59. Structure 60 may, for example be coupled to device 12 by a compression spring 61. Electromagnets 59 may be energized by passing current through a conductor 62 extending from electromagnets 59 through sheath 40 to the proximal end of sheath 40. It should again be understood that the particular electromechanical structure described above is exemplary only and a variety of deformable electromechanical structures could be used to lock sheath 40 and device 12 into position relative to one another. Further, it should be understood that the relative positions of various electromechanical locking components could be reversed as to the sheath 40 and device 12 (e.g., with electromagnets 59 on device 12 engaging ferromagnetic structures 60 on sheath 40).

Accordingly, the present disclosure provides a low-cost and simple method to equip a medical device 12 with a navigation system 10 such that the medical device's 12 physical and cost characteristics are not hindered by the navigation system 10.

Figure 8:
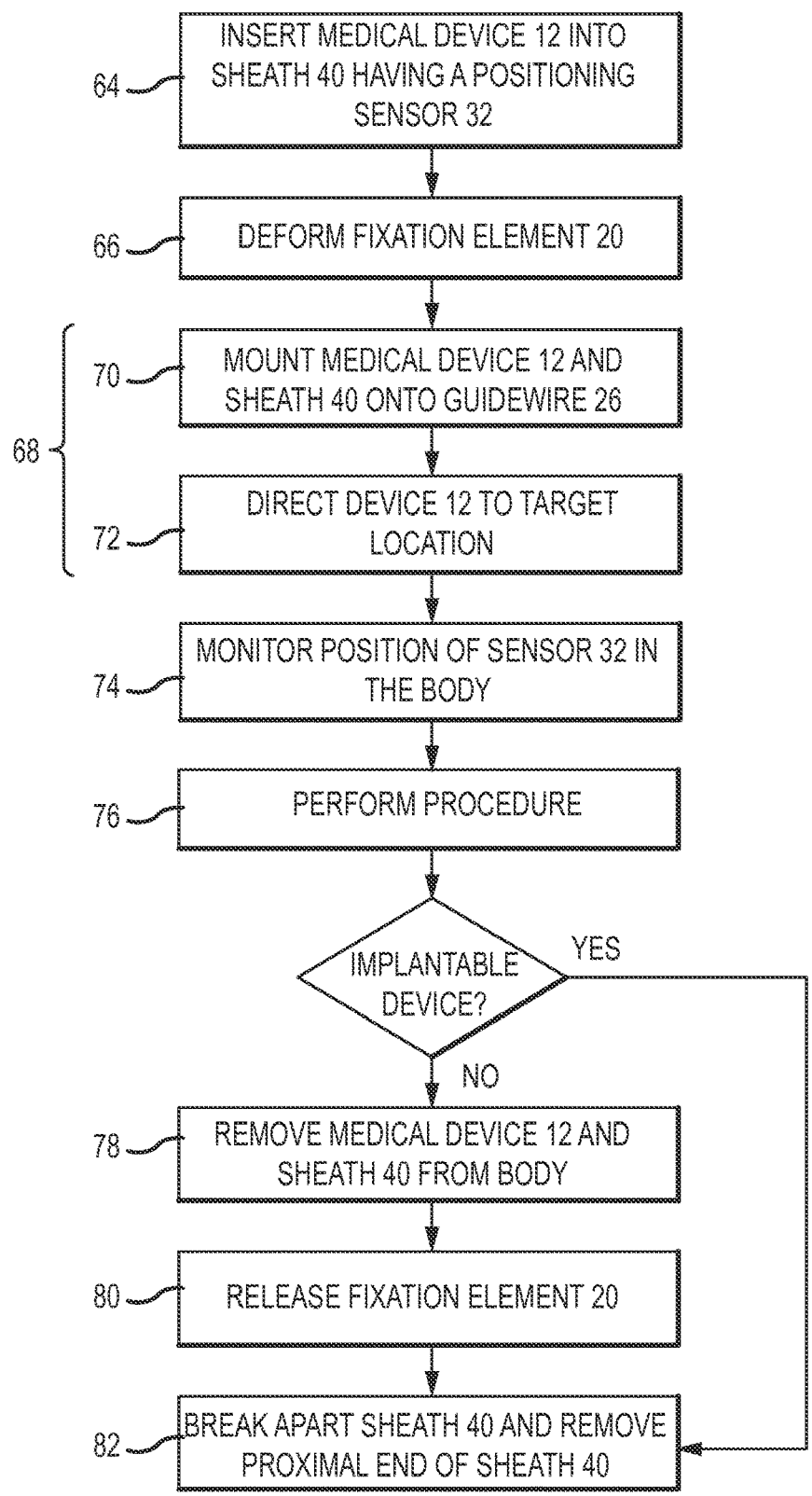
FIG. 8 is a flow chart illustrating one embodiment of a method in accordance with the present disclosure.

Referring now to FIG. 8, the navigation method for a medical device 12 within a body will be described. The method may begin with the step 64 of inserting a medical device 12 into a sheath 40. As noted above, the sheath 40 preferably includes a positioning sensor 32 embedded therein or thereon. The method may continue with the step 66 of deforming a deformable fixation element 20 disposed between the sheath 40 and the medical device 12 to temporarily fix a position of the medical device 12 relative to the sheath 40 and positioning sensor 32. As discussed above fixation element 20 may expand in size or force to prevent relative motion between the sheath 40 and medical device 12. The method may continue with the step 68 of guiding the medical device 12 and sheath 40 to a location within a lumen of a body. As discussed hereinabove, this step may include the substeps 70, 72 of mounting the medical device and the sheath onto a guide wire and directing the medical device 12 to a location within a lumen of a patient's body. The method may further include the step 74 of monitoring a position of the positioning sensor 32 within the body using a conventional navigation system such as the navigation and tracking system sold under the registered trademark "ENSUE NAVX" by St. Jude Medical, Inc. or a magnetic tracking system such as the system sold under the registered trademark "gMPS" by St. Jude Medical Inc.

It should be understood that any of the above-identified fixation elements 20 including shape memory alloy 25 (FIG. 1), pressurized ferrule 48 (FIGS. 2A, 2B and 2C), inflatable balloons 50, 52 (FIG. 3 and FIG. 4), mechanical locking device 54 (FIG. 6) or electromechanical locking device (FIG. 7) may be used in embodiments where sheath 40 covers or encloses medical device 12 (e.g., FIG. 1) or where sheath 40 covers only a portion of medical device 12 (e.g., FIG. 5).

The method may further include the step 76 of performing a medical procedure. Once the medical procedure is completed, if device 12 is not an implantable device, the method may include the step 78 of removing the sheath 40 and medical device 12 from the patient's body and the step 80 of releasing the fixation element. Alternatively, in the case of implanted medical devices 12, once the medical procedure is completed, the method may include the step 82 of separating the sheath 40 and sensor 32 from the device 12 as discussed above.

In yet another alternative method, the sheath may be removed prior to commencing the medical procedure. Therefore, once the medical device is in the desired location, the fixation element may release the sheath and the sheath may be pulled back or perforated and pulled away/removed to allow for treatments such as, but not limited to, a balloon catheter where the inflation of balloon is required for stent placement.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A medical navigation device, comprising:
   a sheath comprising a material, the sheath configured to cover at least a portion of a medical device configured for navigation in a body lumen of a patient, wherein the sheath comprises a first opening, a second opening, and a lumen therebetween, wherein the first opening, the second opening, and the lumen are each sized and configured such that a portion of the medical device may removably pass therethrough; and
   a positioning sensor comprising an electromagnetic coil affixed within the material of the sheath so that the sheath and the positioning sensor are removable from the medical device and from the body lumen while the medical device remains in the body lumen, wherein the electromagnetic coil is sized and configured such that a portion of the medical device may removably pass therethrough, and wherein the electromagnetic coil is electrically coupled to conductors extending longitudinally along the sheath from the electromagnetic coil to a sheath proximal end located outside of the body lumen and patient while the medical device remains in the body lumen so as to enable connection of the conductors to a navigation and tracking system, and wherein the electromagnetic coil is sized and configured to produce a signal that can be interpreted by a signal processing unit and such that a portion of the medical device may pass therethrough.

2. The medical navigation device as defined in claim 1, further comprising a deformable fixation element disposed between the sheath and the medical device, the deformable fixation element configured to be operatively deformed to temporarily fix a position of the medical device relative to the sheath and positioning sensor.

3. The medical navigation device as defined in claim 1 wherein the fixation element comprises an inflatable balloon disposed between the sheath and the medical device.

4. The navigation device as defined in claim 1 wherein the fixation element comprises a shape memory alloy.

5. The medical navigation device as defined in claim 1 wherein the sheath is operatively configured to be separated from the medical device while the medical navigation device and the medical device are both disposed within a lumen in a body, such that the sheath may be removed from the body while the medical device remains disposed within the lumen in the body.

6. The medical navigation device as defined in claim 5 wherein the sheath defines perforations configured to allow portions of the sheath to break away from one another.

7. The medical navigation device as defined in claim 5 wherein the sheath defines a portion that is weakened relative to other portions of the sheath to allow the portion that is weakened to break away from the other portions of the sheath.

8. The medical navigation device of claim 5, wherein the sheath further comprises a weakened area extending longitudinally along the sheath allowing the sheath to be broken apart, wherein the sheath further comprises an extended section that is sized and configured to remain outside a patient's body, and wherein, upon application of a force to the extended section, the sheath may be broken away from the medical device along the weakened area.

9. The medical navigation device as defined in claim 1 wherein the portion of the medical device comprises a portion of the distal end of the medical device.

10. The medical navigation device as defined in claim 1, wherein the signal comprises an induced voltage when the electromagnetic coil is subject to an external magnetic field.

11. The medical navigation device as defined in claim 1, wherein the signal is interpretable by the signal processing unit to determine a location of the electromagnetic coil relative to a navigation and tracking system.

12. The medical navigation device as defined in claim 11 wherein the signal processing unit is connected to the navigation and tracking system, and wherein the navigation and tracking system is configured to measure an induced voltage produced by the electromagnetic coil.

13. The medical navigation device as defined in claim 1, wherein the conductors extend within the material of the sheath from the electromagnetic coil to the sheath proximal end.

14. The medical navigation device of claim 1, wherein the electromagnetic coil is embedded within the material of the sheath.

15. The medical navigation device of claim 1, wherein the electromagnetic coil is disposed within the material of the sheath.

16. The medical navigation device of claim 1, wherein the medical device is a guide wire.

17. The medical navigation device of claim 1, wherein the medical device is selected from the group consisting of a catheter, a guide wire, an electrical lead, a stent, a stylet, and a needle.

18. The medical navigation device of claim 1, wherein the medical device is configured to engage a guide wire.

19. A navigation method for a medical device within a body, the navigation method comprising the steps of:
    inserting the medical device into a sheath comprising a material and having a positioning sensor affixed within the material of the sheath so that the sheath and the positioning sensor are removable from the medical device and the body while the medical device remains within the body, the positioning sensor comprising an electromagnetic coil located within the sheath and sized and configured such that a portion of the medical device may removably pass through the electromagnetic coil, and wherein the electromagnetic coil is electrically coupled to conductors extending longitudinally along the sheath from the electromagnetic coil to a sheath proximal end located outside of the body;
    deforming a deformable fixation element disposed between the sheath and the medical device to temporarily fix a position of the medical device relative to the sheath and positioning sensor;
    guiding the medical device and sheath to a location within a lumen of a body; and
    monitoring a position of the positioning sensor within the body to thereby monitor a position of the medical device during navigation of the medical device within the body.

20. The navigation method as defined in claim 19, further comprising the step of separating the sheath from the medical device while the sheath and medical device are disposed within the body.

21. The navigation method as defined in claim 19 wherein the medical device is a catheter.

22. The navigation method as defined in claim 19 wherein the medical device is a guide wire.

23. The navigation method as defined in claim 19 wherein the medical device is a stent.

24. The navigation method as defined in claim 19 wherein the sheath is tubular and disposed about the medical device.

25. The navigation method as defined in claim 19 wherein the fixation element comprises an inflatable balloon disposed between the sheath and the medical device.

26. The navigation method as defined in claim 19 wherein the fixation element comprises a shape memory alloy.

27. The navigation method as defined in claim 19, wherein the deformable fixation element engages the sheath and the medical device to temporarily fix the position of the medical device at least partially within the sheath.

* * * * *